United States Patent [19]

Denny

[11] Patent Number: 4,870,976

[45] Date of Patent: Oct. 3, 1989

[54] INTRAVENOUS INJECTION SHIELD ASSEMBLY

[76] Inventor: Thomas A. Denny, 3609 Crescent Ave., Farmington, N. Mex. 87401

[21] Appl. No.: 101,827

[22] Filed: Sep. 28, 1987

Related U.S. Application Data

[63] Continuation-in-part of Ser. No. 923,616, Oct. 27, 1986, abandoned.

[51] Int. Cl.[4] ............................................. A61F 13/00
[52] U.S. Cl. .................................... 128/877; 128/888; 128/DIG. 6
[58] Field of Search ................. 128/133, 134, DIG. 6, 128/DIG. 26, 877, 878, 879

[56] References Cited

U.S. PATENT DOCUMENTS

| | | | |
|---|---|---|---|
| 2,763,264 | 9/1956 | McInnerny | 128/DIG. 6 |
| 2,831,487 | 4/1958 | Tafilaw | 604/174 |
| 2,858,540 | 11/1958 | Morrison | 128/80 C |
| 3,059,645 | 10/1962 | Hasbrouck et al. | 128/133 |
| 3,194,235 | 7/1965 | Cooke | 128/DIG. 26 |
| 3,256,880 | 6/1966 | Caypinar | 128/877 |
| 3,521,625 | 7/1970 | Mackey | 128/DIG. 6 |
| 3,640,273 | 2/1972 | Ray | 128/87 R |
| 3,722,508 | 3/1973 | Roberts | 128/DIG. 6 |
| 3,782,377 | 1/1974 | Rychlik | 128/DIG. 6 |
| 3,788,307 | 1/1974 | Kistner | 128/77 |
| 3,831,467 | 8/1974 | Moore | 128/80 C |
| 3,901,226 | 8/1975 | Scardenzan | 128/DIG. 6 |
| 4,254,766 | 3/1981 | Kordis | 128/133 |
| 4,265,232 | 5/1981 | Stonich | 128/133 |
| 4,286,588 | 9/1981 | Lovegrove | 128/133 |
| 4,290,425 | 9/1981 | Helfer et al. | 128/877 |
| 4,316,461 | 2/1982 | Marais et al. | 128/133 |
| 4,397,647 | 8/1983 | Gordon | 604/8 |
| 4,449,975 | 5/1984 | Perry | 604/179 |
| 4,470,410 | 9/1984 | Elliott | 128/133 |
| 4,517,971 | 5/1985 | Sorbonne | 128/133 |
| 4,561,857 | 12/1985 | Sacks | 128/DIG. 6 |
| 4,591,356 | 5/1986 | Christie | 128/DIG. 26 |

FOREIGN PATENT DOCUMENTS

2148123 5/1985 United Kingdom ................ 128/877

Primary Examiner—Robert A. Hafer
Assistant Examiner—Charles H. Sam
Attorney, Agent, or Firm—Emch, Schaffer, Schaub & Porcello Co.

[57] ABSTRACT

An improved intravenous injection shield assembly is disclosed. The assembly includes a protective shield member made of a rigid transparent plastic material. The assembly further includes strap members for holding the assembly in a predetermined position on a limb. The assembly when positioned on the limb is longitudinally extending with respect to the limb to prevent the bending of the limb. When the shield is positioned on the limb, a space is defined between the uppermost surface of the shield member and the upper surface of the limb. An intravenous needle and tubing can be positioned in the space between the shield member and the limb.

28 Claims, 5 Drawing Sheets

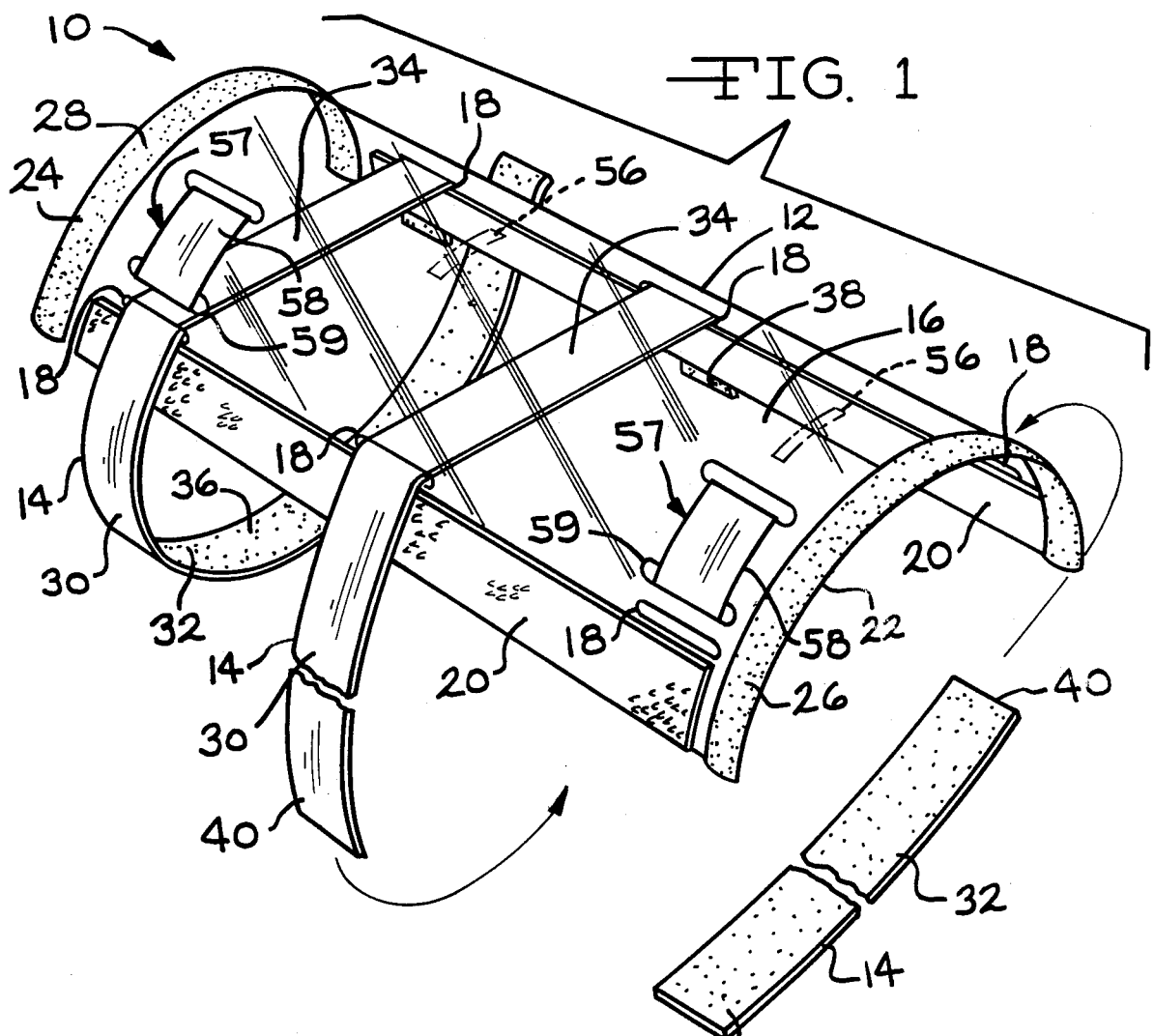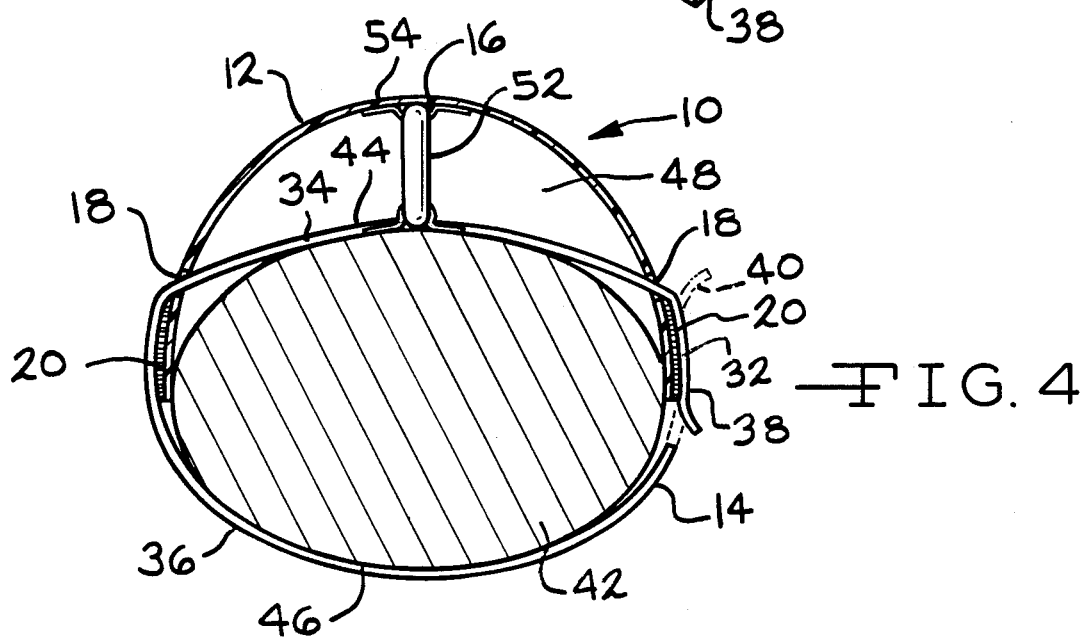

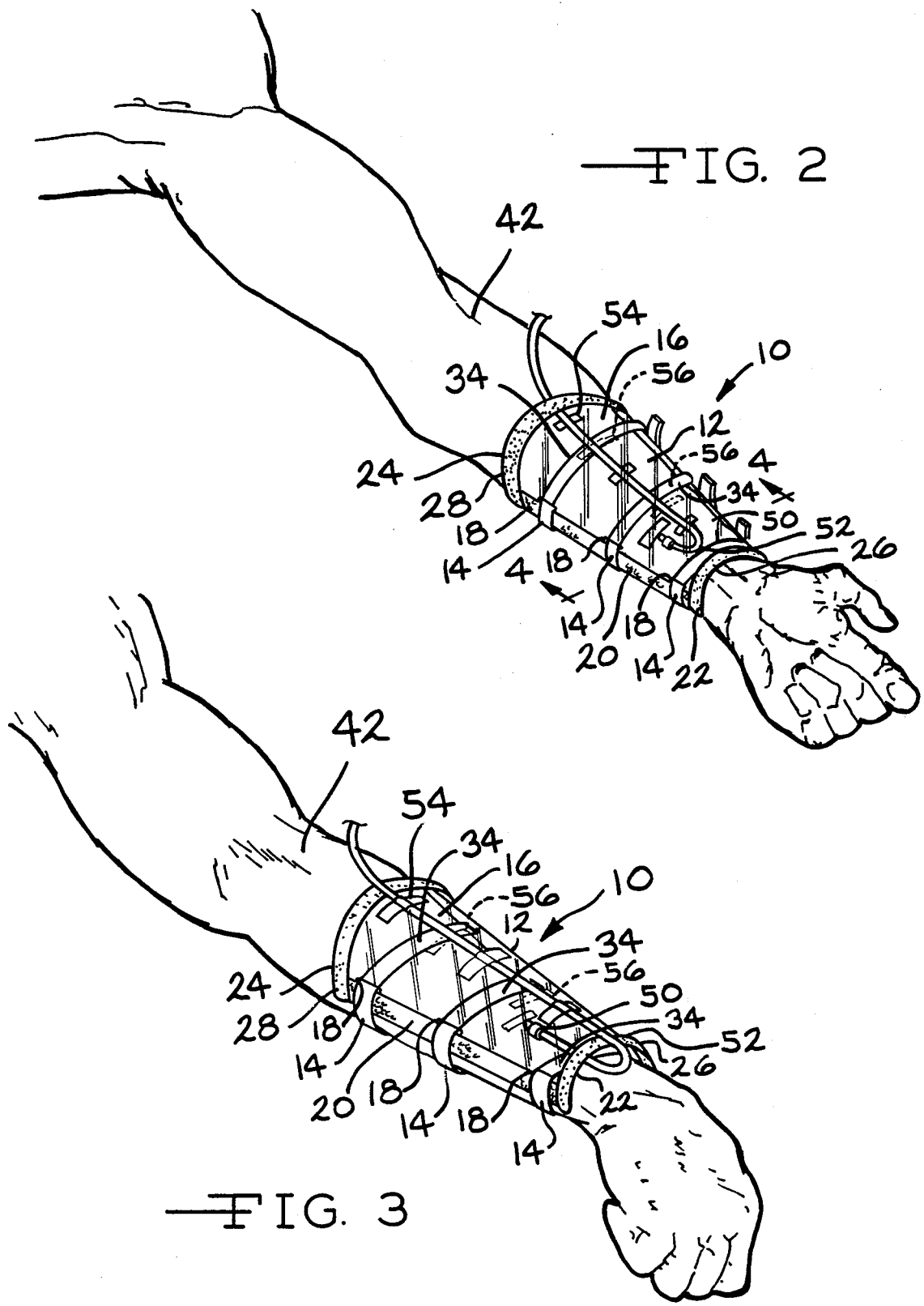

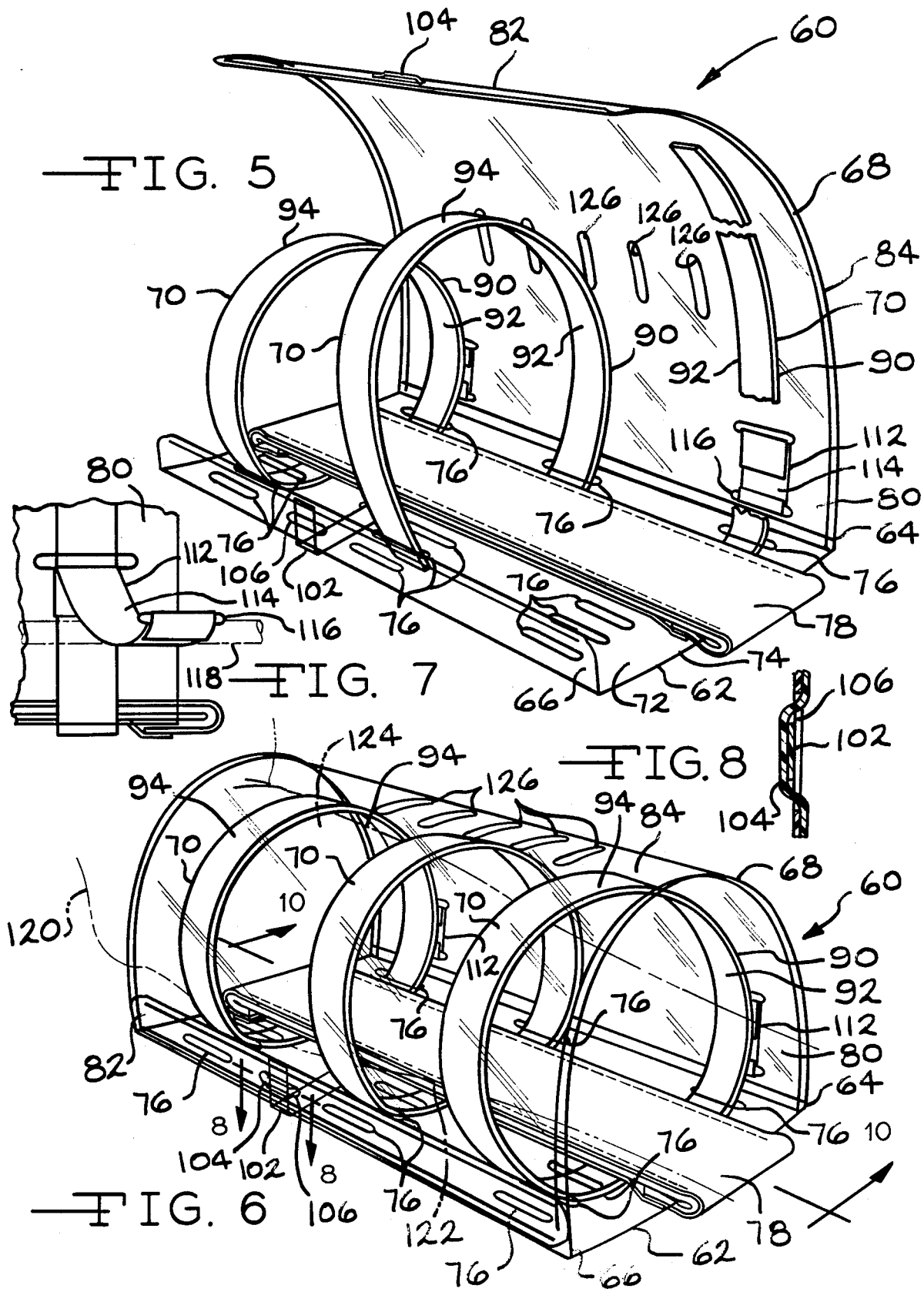

INTRAVENOUS INJECTION SHIELD ASSEMBLY

BACKGROUND OF THE INVENTION

The invention relates generally to an intravenous injection shield assembly. More specifically, the invention is directed to a light weight assembly which includes a transparent shield made of a plastic material and straps to be wrapped around a limb. The assembly is positioned on a limb over the area of skin where an intravenous needle has been inserted. The assembly protects against the inadvertent removal or jarring of the needle which can be painful to a person whose limb is subjected to the needle.

SUMMARY OF THE INVENTION

The present invention relates to an improved intravenous injection shield assembly for a limb. The first embodiment of the invention is an assembly which includes a protective shield member made of a rigid transparent plastic material. The shield member defines openings spaced from the uppermost surface of the shield. The assembly further includes at least two strap members which extend through the openings defined in the shield member. In the first embodiment, each strap member has an upper limb portion and a lower limb portion. Synthetic materials which adhere when pressed together, such as "VELCRO", are positioned on each of the strap members and on the shield member for holding the assembly in a predetermined position on the limb.

The first embodiment assembly is positioned on the limb by placing the upper limb portion of each strap member adjacent to the upper surface of the limb and wrapping the lower limb portion of each strap member around the limb adjacent to the bottom surface of the limb. The synthetic materials which are positioned on the strap members and the shield member are then pressed together so that the assembly is retained on the limb. The assembly when positioned on the limb is longitudinally extending with respect to the limb in order to prevent the bending of the limb.

After the assembly is positioned on the limb, a space is defined between the uppermost surface of the shield member and the upper surface of the limb. An intravenous needle and tubing can be positioned in the space defined by the shield member and the limb. The shield assembly protects against the inadvertent removal or jarring of the needle.

The second embodiment of the invention is an assembly which includes a base member having an upper surface and a lower surface. The base member defines a plurality of strap openings. The second embodiment assembly further includes a first side wall and a second side wall which are joined to the upper surface of the base member in an opposed relationship to one another. A protective shield member having an uppermost surface, a first edge and a second edge is joined to the first side wall along its first edge. The base member, first and second side walls and protective shield member are made of a rigid plastic material. The assembly further includes at least two strap members each having a limb contact portion and a base contact portion. Each of the strap members extends through the strap openings defined by the base member. Synthetic materials which adhere when pressed together, such as "VELCRO", are positioned on each of the strap members and the lower surface of the base member for holding the assembly in a predetermined position on the limb.

The second embodiment assembly is positioned on the limb by placing the upper surface of the base member adjacent to the lower surface of the limb. The strap members are then extended through the strap openings which are defined by the base member. The strap members are wrapped around the limb so that the limb contact portions of the strap members are in contact with the upper surface of the limb and the base member contact portions of the strap members are in contact with the lower surface of the base member. The synthetic materials which are positioned on the strap members and base member are then pressed togehthr so that the assembly is retained on the limb. The protective shield member is positioned over the upper surface of the limb by placing the second edge of the shield member adjacent to the second side wall. The uppermost surface of the protective shield member is held in a spaced apart relationship with the upper surface of the limb. An intravenous needle and tubing can be positioned in the space defined by the shield member and the limb.

The third embodiment of the invention is an assembly which includes a base member having an upper surface and a lower surface. The base member defines a plurality of strap openings. The third embodiment assembly further includes a first side wall and a second side wall. The first and second side walls are joined to the upper surface of the base member in an opposed relationship to one another. The assembly further includes a protective shield member having an uppermost surface, a first edge and a second edge. The base member, first and second side walls and protective shield member are made of a rigid plastic material. The assembly has at least two strap members each having a limb contact portion and a base member contact portion. Each of the strap members extends through the strap openings defined by the base member. Synthetic materials which adhere when pressed together, such as "VELCRO", are positioned on each of the strap members and the lower surface of the base member for holding the assembly in a predetermined position on the limb.

The third embodiment assembly is positioned on the limb by placing the upper surface of the base member adjacent to the lower surface of the limb. The strap members are then extended through the strap openings which are defined by the strap openings. The strap members are wrapped around the limb so that the limb contact portions of the strap members are in contact with the upper surface of the limb and the base member contact portions of strap members are in contact with the lower surface of the base member. The synthetic materials which are positioned on the strap members and the base member are then pressed together so that the assembly is retained on the limb. The protective shield member is positioned over the upper surface of the limb by placing the first edge and the second edge of the shield member adjacent to the first side wall and the second side wall, respectively. The uppermost surface of the protective shield member is held in a spaced apart relationship with the upper surface of the limb. An intravenous needle and tubing can be positioned in the space defined by the shield and the limb.

A principal object of the present invention is to provide a novel intravenous injection shield assembly that protects against the inadvertent removal or jarring of an intravenous needle which has been placed in the limb of a person.

An important object of the present invention is to provide an assembly which can be easily placed on the limb of a person.

Another important object of the present invention is to provide an assembly that prevents the bending of a limb which is attached to an intravenous needle.

Other objects and advantages of the invention will become apparent as the invention is described hereinafter in detail with reference being made to the accompanying drawings.

BRIEF DESCRIPTION OF THE DRAWINGS

FIG. 1 is a perspective view of the first embodiment of the shield assembly according to the present invention;

FIG. 2 is a pictorial view of a person's arm in the supine position with the first embodiment of the shield assembly according to the present invention attached thereto;

FIG. 3 is a pictorial view of a person's arm in the prone position with the first embodiment of the shield assembly according to the present invention attached thereto;

FIG. 4 is a cross sectional view taken along line 4—4 of FIG. 2;

FIG. 5 is a perspective view of the second embodiment of the shield assembly according to the present invention with the protective shield member in an open position;

FIG. 6 is a pictorial view of a person's arm in the prone position shown in dashed lines with the second embodiment of the shield assembly according to the present invention attached thereto;

FIG. 7 is a side elevational view of the intravenous tubing retainer means according to the present invention;

FIG. 8 is a cross sectional view of the closure means according to the present invention taken along lines 8—8 of FIG. 6;

DETAILED DESCRIPTION OF THE PREFERRED EMBODIMENTS

Figure 9:
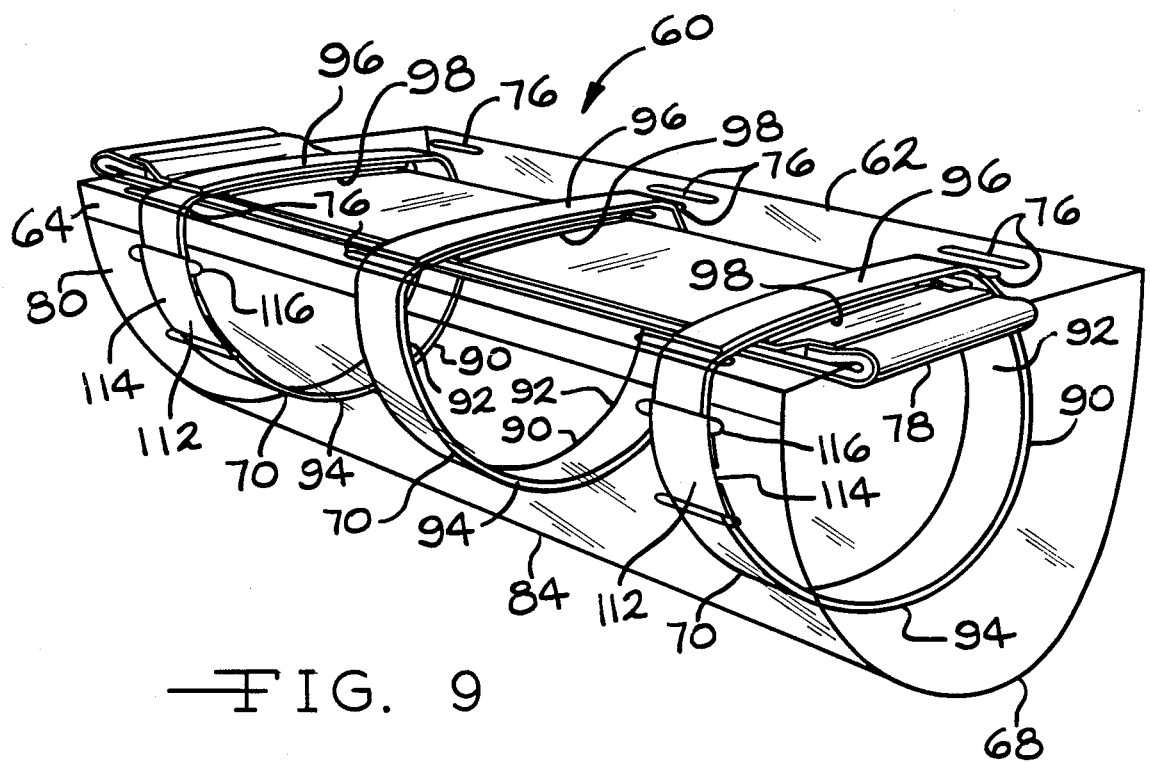
FIG. 9 is a perspective view of the second embodiment of the shield assembly according to the present invention.

Referring now to the drawings, the first embodiment of the shield assembly constructed in accordance with the present invention is indicated generally by the reference numeral 10. The shield assembly 10, as shown in FIG. 1, includes a protective shield member 12. As shown in this embodiment, the shield member 12 is generally semi-cylindrical in shape. However, the shield member in other embodiments can be formed into a variety of shapes. For example, the shield member can include a flat top surface with depending walls which are also flat and extending downwardly and outwardly from the edges of the flat top surface (not shown). The shield assembly further includes strap members 14. The first embodiment includes three strap members 14. However, two strap members can be used for a small shield assembly.

Referring still to FIG. 1, the shield member 12 consists of a rigid transparent plastic material. The shield member 12 has an uppermost surface 16. The shield member 12 defines strap openings 18 which are spaced from the uppermost surface 16 of the shield member 12. Shield fastening means 20 made of a synthetic material, such as "VELCRO", are attached to the shield member 12 spaced from the uppermost surface 16 near the strap openings 18. The shield member 12 includes a first end portion 22 and a second end portion 24. A first fabric protection pad 26 and a second fabric protection pad 28 are mounted on the first and second end portions 22 and 24, respectively, for the comfort and protection of the person using the assembly 10. Fabric protection pads can also be mounted along the interior edges of the shield member for additional comfort and protection (not shown).

Referring still to FIG. 1, the strap members 14 consist of a woven material 30 attached to strap fastening means 32 made of a synthetic material, such as "VELCRO". The strap members 14 extend through the strap openings 18 defined by shield member 12. Each of the strap members 14 includes an upper limb portion 34 and a lower limb portion 36. Each of the strap members 14 further includes a first end 38 and a second end 40.

The positioning of the shield assembly 10 on a person's limb is shown in FIGS. 2, 3 and 4. The person's limb, in this case an arm, is indicated by the reference number 42. It should be understood that the assembly 10 can also be positioned on a person's leg.

FIGS. 2 and 3 show the positioning of the assembly 10 on a person's arm 42. FIG. 2 shows the assembly 10 placed on an arm 42 which is in the supine position. FIG. 3 shows the assembly 10 placed on an arm 42 which is in the prone position.

The positioning of the assembly 10 on an arm 42 is best shown in FIGS. 1 and 4. The strap fastening means 32 of the first end 38 of each strap member 14 is attached to the shield fastening means 20. Each of the strap members 14 extends through its corresponding strap openings 18. The individual strap members 14 are then wrapped around the arm 42. The strap fastening means 32 of the second end 40 of each strap member 14 is attached to the same shield fastening means 20 to which the first end 38 is attached. When the assembly 10 is positioned on an arm 42, the upper limb portion 34 of the strap members 14 is adjacent to the upper surface 44 of the arm 42 and the lower limb portion 36 of the strap members 14 is adjacent to the bottom surface 46 of the arm 42. The assembly 10 is positioned longitudinally extending with respect to the arm 42 to prevent the bending of the arm.

Referring to FIGS. 2, 3 and 4, a space 48 is defined between the uppermost surface 16 of the shield member 12 and the upper surface 44 of the arm 42. An intravenous needle 50 and tubing 52 can be positioned in the space 48. The tubing is held to either the shield member 12 or the upper surface 44 of the arm 42 by tape 54.

Air openings 56 are defined by the shield member 12 at its uppermost surface 16. The air openings 56 allow air to pass through the openings into the space 48 defined by the shield member 12 and the upper surface 44 of the arm 42.

The assembly 10 can also include intravenous tubing retaining means 57 as shown in FIG. 1. The retaining means 57 includes at least one adhesive strip 58 which can be removably attached to the exterior surface of the shield member 12. The retaining means 57 further includes a tab 59 for handling. An intravenous tube can be positioned between the adhesive strip 58 and the shield member 12.

The second embodiment of a shield assembly constructed in accordance with the present invention is indicated generally by the reference numeral 60. The shield assembly 60 is shown in FIGS. 5, 6, 9 and 10. The assembly 60 generally includes a base member 62, a first side wall 64, a second side wall 66, a protective shield member 68 and at least two strap members 70.

Figure 10:
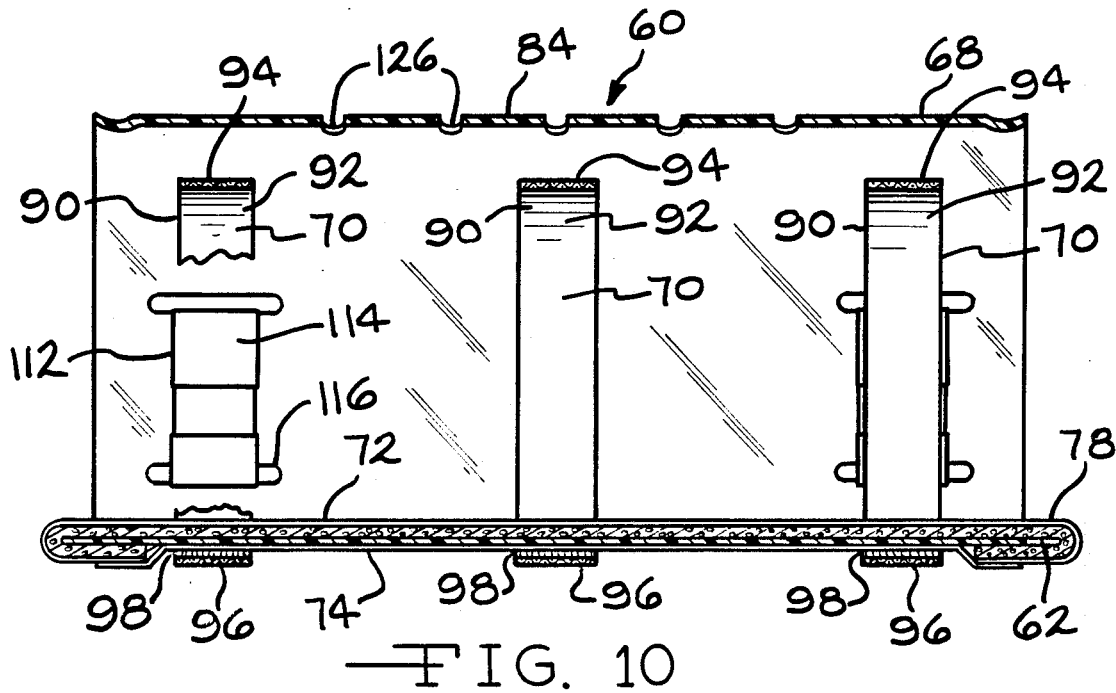
FIG. 10 is a sectional view of the second embodiment of the shield assembly according to the present invention as shown in FIG. 9.

Referring to FIGS. 5, 9 and 10, the base member 62 has an upper surface 72 and a lower surface 74. The base member 62 defines a plurality of strap openings 76. The strap openings 76 receive the strap members 70. A fabric protection pad 78 can be mounted on the upper surface 72 of the base member 62 to protect the limb of the user of the assembly. The base member is usually formed of a rigid plastic material which is transparent.

The first side wall 64 and the second side wall 66 are shown in FIGS. 5, 6, 9 and 10. The first side wall 64 and the second side wall 66 are joined to the upper surface 72 of the base member 62 in an opposed relationship to one another. The side walls are usually formed from a rigid transparent plastic material.

Referring to FIGS. 5, 6 9 and 10, the protective shield member 68 is shown. The protective shield member 68 includes a first edge 80 and a second edge 82. The first edge 80 is joined to the first side wall 64. The shield member 68 also includes an uppermost surface 84. As shown in the second embodiment, the shield member 68 is generally semi-cylindrical in shape. However, the shield member can be formed in a variety of shapes. For example, the shield member can include a flat top surface with depending walls which are also flat and extending downwardly and outwardly from the edges of the flat top (not shown). The protective shield member 68 is usually formed from a rigid transparent plastic material.

Referring to FIG. 5, the second embodiment includes three strap members 70. However, two strap members can be used for a small shield assembly. Referring still to FIG. 5, the strap members 70 consist of a woven material 90 attached to the strap fastening means 92 made of a synthetic material, such as "VELCRO". The strap members 70 extend through the strap openings 76 defined by the base member 62. Referring to FIG. 9, each of the strap members 70 includes a limb contact portion 94 and a base member contact portion 96. As shown in FIGS. 9 and 10, the strap fastening means 92 of the strap members 70 adhere to base member fastening means 98 made of a synthetic material, such as "VELCRO". The strap fastening means 92 and the base member fastening means 98 when pressed together act to hold the shield assembly 60 in a predetermined position on the limb.

Referring to FIGS. 6 and 8, the closure means 100 is shown. The closure means 100 includes a latch 102, a cavity 104 and a closure opening 106. The L-shaped latch 102 is positioned on the lower surface 74 of the base member 62. The cavity 104 is defined by the second edge 82 of the protective shield member 68. The closure opening 106 is defined by the second side wall 66. As shown in FIGS. 6 and 8, the closure means acts to hold the second edge 82 of the protective shield member 68 adjacent to the second side wall 66. This is accomplished when the cavity 104 is inserted through the opening 106 and the latch 102 is positioned in the cavity 104.

The intravenous tubing retaining means 112 is best shown in FIGS. 7 and 10. The retaining means 112 includes at least one adhesive strip 114 which can be removably attached to the first edge 80 of the protective shield member 68. The retaining means 112 further includes a tab 116 for handling. An intravenous tube 116 can be positioned between the adhesive strip 114 and the protective shield member 68.

The positioning of the second embodiment assembly 60 on the person's limb is shown in FIG. 6. The person's limb, in this case an arm, is indicated by the reference numeral 120. The assembly can also be positioned on a person's leg. The assembly can be placed on a limb which is either in the prone or supine position.

FIG. 6 shows the assembly 60 placed on an arm 120 which is in the prone position. The arm 120 is placed on the upper surface 72 of the base member 62 adjacent to the lower surface of the arm 122. The strap members 70 are extended through the strap openings 76. The strap members 70 are wrapped around the arm 120 so that the limb contact portions 94 are in contact with the upper surface of the arm 124. The base member contact portions 98 are in contact with the lower surface 74 of the base member 62. The strap fastening means 92 are then pressed together with the base member fastening means 98 in order to retain the assembly 60 on the arm 120. The assembly 60 is positioned longitudinally extending with respect to the arm 120 to prevent the bending of the arm.

After the assembly 60 has been secured to the arm 120, the protective shield member 68 is then positioned over the upper surface of the arm 124 by placing the second edge 82 of the shield member 68 adjacent to the second side wall 66. The latch 102 is then positioned in the cavity 104 to hold the shield member 68 in place.

When the shield member 68 is positioned over the upper surface of the arm 124, the uppermost surface 84 of the shield member 68 is held in a spaced apart relationship with the upper surface of the arm 124. An intravenous needle and tubing can be positioned in the space defined by the shield member 68 and the arm 120.

Air openings 126 are defined by the shield member 68 at the uppermost surface 84. The air openings 126 allow air to pass through the openings into the space defined by the shield member and the upper surface of the arm 124.

Figure 11:
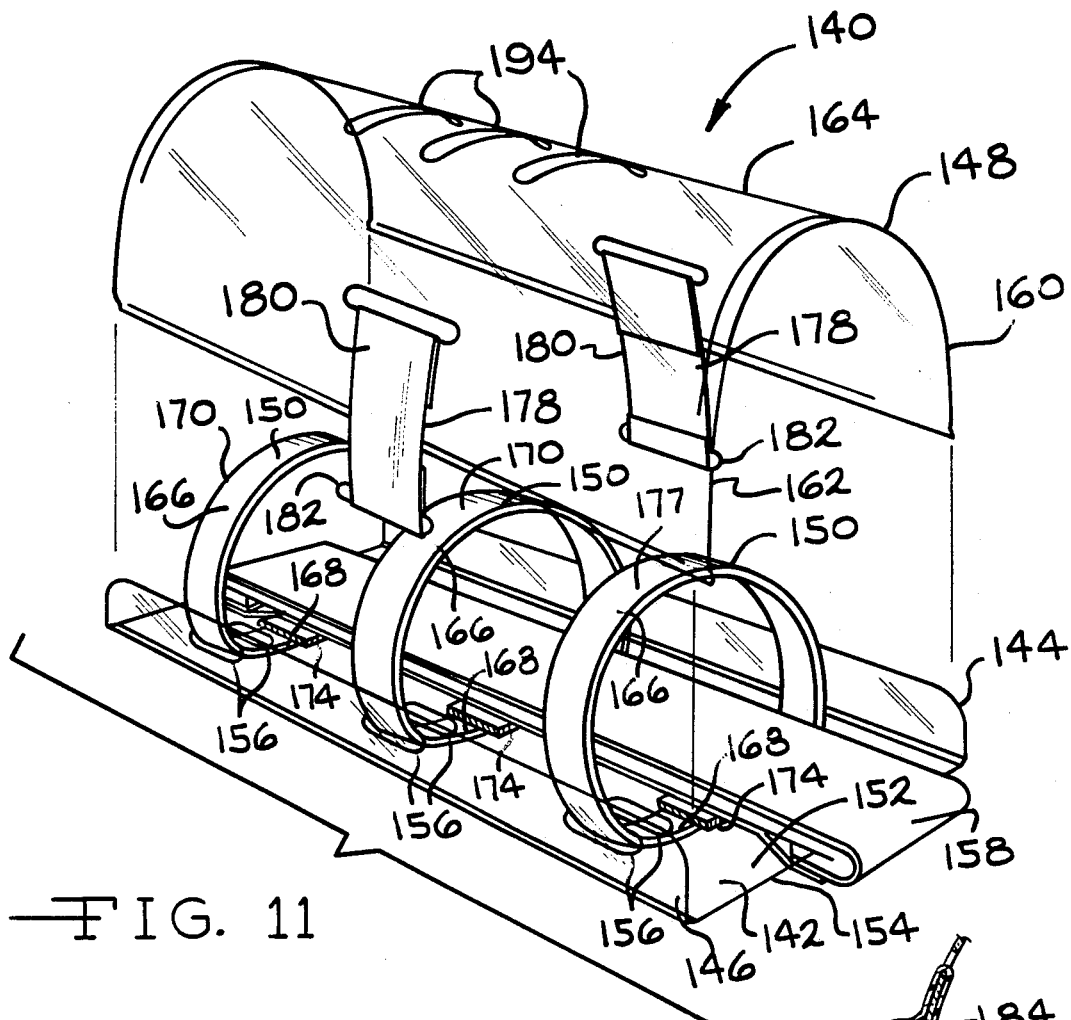
FIG. 11 is a perspective view of the third embodiment of the shield assembly according to the present invention.
Figures 12, 13:
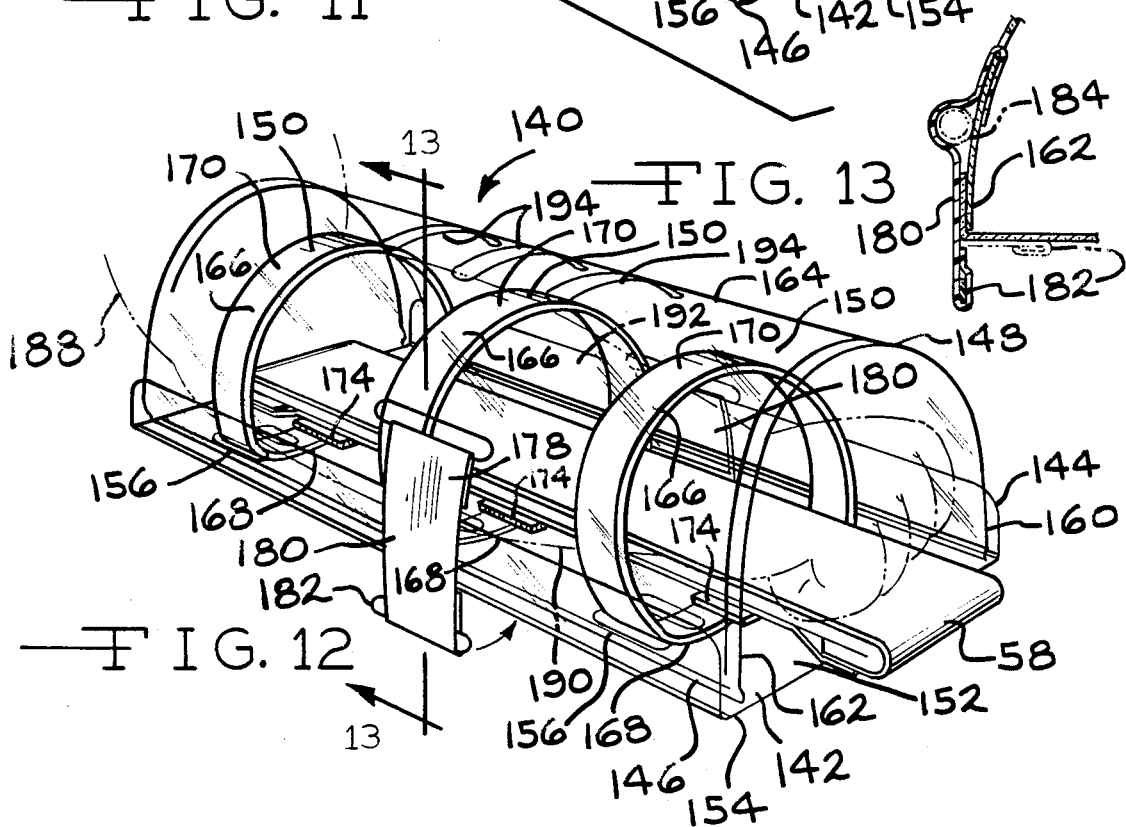
FIG. 12 is a pictorial view of a person's arm in the prone position shown in dashed lines with the third embodiment of the shield assembly according to the present invention attached thereto.
FIG. 13 is a cross sectional view of the closure means according to the present invention taken along lines 13—13 of FIG. 12.

The third embodiment of a shield assembly constructed in accordance with the present invention is indicated generally by the reference numeral 140. The shield assembly 140 is shown in FIGS. 11 and 12. The assembly 140 generally includes a base member 142, a first side wall 144, a second side wall 146, a protective shield member 148 and at least two strap members 150.

Referring to FIG. 5, the base member 142 has an upper surface 152 and a lower surface 154. The base member 142 defines a plurality of strap openings 156. The strap openings 156 receive the strap members 150. A fabric protection pad 158 can be mounted on the upper surface 152 of the base member 142 to protect the limb of the user of the assembly. The base member is usually formed of a rigid transparent plastic material.

The first side wall 144 and the second side wall 146 are shown in FIGS. 11 and 12. The first side wall 144 and second side wall 146 are joined to the upper surface 152 of the base member 142 in an opposed relationship to one another. The side walls are usually formed of a rigid transparent plastic material.

Referring to FIGS. 11 and 12, the protective shield member 148 is shown. The protective shield member 148 includes a first edge 160 and a second edge 162. The shield member 148 also includes an uppermost surface 164. As shown in the third embodiment, the shield member 148 is generally semi-cylindrical in shape. However, the shield member can be formed in a variety of shapes. For example, the shield member can include a flat top surface with depending walls which are also flat and extending downwardly and outwardly from the edges of the flat top (not shown). The protective shield member 148 is usually formed from a rigid transparent plastic material.

Referring to FIG. 11, the third embodiment includes three strap members 150. However, two strap members can be used for a small shield assembly. Referring still to FIG. 11, the strap members 150 consist of a woven material 166 attached to strap fastening means 168 made of a synthetic material, such as "VELCRO". The strap members 150 extend through the strap openings 156 defined by base member 142. Each of the strap members 150 includes a limb contact portion 170 and a base member contact portion 172. The strap fastening means 168 of the strap member 150 adhere to base member fastening means 174 made of synthetic material, such as "VELCRO", which are mounted on the lower surface 154 of the base member 142. The strap fastening means 168 and base member fastening means when pressed together act to hold the shield assembly 140 in a predetermined position on the limb.

Referring to FIGS. 11, 12 and 13, the closure means 178 are shown. The closure means 178 consist of adhesive strips 180 removably attached to the first edge 160 and the second edge 162 of the shield member 148. The closure means 178 further include tabs 182 for handling. As shown in FIG. 13, the closure means 178 act to hold the first edge 160 and second edge 162 of the protective shield member 148 adjacent to the first side wall 144 and the second side wall 146, respectively. This is accomplished when the adhesive strips 180 are adhered to the first side wall 144 and second side wall 146. The adhesive strips 180 can also act to retain an intravenous tube 184 as shown in FIG. 13.

The positioning of the second embodiment assembly 140 on a persons's limb is shown in FIG. 12. The person's limb, in this case an arm, is indicated by the reference numeral 188. The assembly can also be positioned on a person's leg. The assembly can be placed on a limb which is either in the prone or supine position.

FIG. 12 shows the assembly 140 placed on an arm 188 which is in the prone position. The arm 188 is placed on the upper surface 152 of the base member 142 adjacent to the lower surface of the limb 190. The strap members 150 are extended through the strap openings 156. The strap members 150 are then wrapped around the arm 188 so that the limb contact portions 170 of the strap members 150 are in contact with the upper surface of the limb 192. The base member contact portions 172 are in contact with the lower surface 154 of the base member 142. The strap fastening means 168 are then pressed together with the base member fastening means 174 in order to retain the assembly 140 on the arm 188. The assembly 140 is positioned longitudinally extending with the respect to the arm 188 to prevent the bending of the arm.

After the assembly 140 has been secured to the arm 188, the protective shield member 148 is then positioned over the upper surface of the arm 192 by placing the first edge 160 and the second edge 162 of the shield member 148 adjacent to the first side wall 144 and the second side wall 146, respectively. The adhesive strips 180 are then positioned against the first side wall 144 and second side wall 146 to hold the shield member 148 in place.

When the shield member 148 is positioned over the upper surface of the arm 192, the uppermost surface 164 of the shield member 148 is held in a spaced apart relationship with the upper surface of the arm 192. An intravenous needle and tubing can be positioned in the space defined by the shield member 148 and the arm 188.

Air openings 194 are defined by shield member 148 at the uppermost surface 164. The air openings 194 allow air to pass through the openings into the space defined by the shield member and the upper surface of the arm.

It should be understood that many changes may be made to the structure disclosed in the drawings and still fall within the scope of the following claims.

I claim:

1. An improved intravenous injection shield assembly for positioning on a limb comprising, in combination:

a laterally flexible protective shield member adaptable for secure positioning along the sides of such limb, said shield member having an arcuate surface, said surface extending from opposed free ends to a central uppermost point of said shield, said shield defining a plurality of strap openings spaced from the uppermost surface of said shield member;

at least two adjustable strap members each having an upper limb portion and a lower portion, each of said strap members extending through said strap openings;

whereby said portion of each of said strap members which is adapted for contact with the upper portion of such limb is in contact with the upper surface of such limb and said portion of each of said strap members which is adapted for contact with the lower portion of such limb is in contact with the lower surface of such limb, said uppermost surface of said shield member being held in a spaced apart relationship with the upper surface of such limb such that an intravenous needle and tubing can be positioned in the space defined between the uppermost surface of said shield member and the upper surface of such limb; and fastening means postioned on each of said strap members and said shield member for holding the shield assembly in a predetermined position on such limb.

2. The intravenous injection shield assembly of claim 1, wherein said protective shield member consists of a rigid transparent plastic material.

3. The intravenous injection shield assembly of claim 1, wherein said protective shield member includes a first end portion and a second end portion, said first and second end portions having fabric protection pads mounted thereon to protect such limb.

4. The intravenous injection shield assembly of claim 1, wherein said protective shield member includes at least one opening on said uppermost surface of said shield member, said opening allowing air to pass through said opening into the space defined between the uppermost surface of said shield member and the upper surface of such limb.

5. The intravenous injection shield assembly of claim 1, wherein said assembly is longitudinally extending with respect to such limb to prevent bending of such limb.

6. The intravenous injection shield assembly of claim 1, wherein said fastening means consist of synthetic materials which adhere when pressed together.

7. The intravenous injection shield assembly of claim 1, wherein said assembly further includes intravenous tubing retaining means.

8. The intravenous injection shield assembly of claim 7, wherein said intravenous tubing retaining means includes at least one adhesive strip removably attached to said protective shield member.

9. An improved intravenous injection shield assembly for positioning on a limb comprising, in combination:
a base member having a substantially planar upper surface and a lower surface, said base member defining a plurality of strap openings;
a first side wall and a second side wall, said first and second side walls each being joined to said upper surface of said base member in an opposed relationship to one another;
a laterally flexible protective shield member having an uppermost surface, a first edge and a second edge, said first edge being joined to said first side wall;
at least two adjustable strap members each having a limb contact portion and a base member contact portion, each of said strap members extending through said plurality of strap openings;
fastening means positioned on each of said strap members and said base member for holding the shield assembly in a predetermined position on such limb;
whereby when the shield assembly is positioned on such limb, said portions of said strap members which are adapted for contact with the upper surface of such limb are in contact with the upper surface of such limb and said base member contact portions of said strap members are in contact with the lower surface of said base member, said second edge of said protective shield member is adjacent to said second side wall, said protective shield member is positioned over the upper surface of such limb, said uppermost surface of said protective shield member being in a spaced apart relationship with the upper surface of such limb such that an intravenous needle and tubing can be positioned in the space defined between the uppermost surface of said protective shield member and the upper surface of such limb.

10. The intravenous injection shield assembly of claim 9, wherein said base member, first and second side walls and protective shield member consist of a rigid transparent plastic material.

11. The intravenous injection shield assembly of claim 9, wherein a fabric protection pad is mounted on said upper surface of said base member to protect such limb.

12. The intravenous injection shield assembly of claim 9, wherein said protective shield member includes at least one opening on said uppermost surface of said shield member, said opening allowing air to pass through said opening into the space defined between the uppermost surface of said shield member and the upper surface of such limb.

13. The intravenous injection shield assembly of claim 9, wherein said assembly is longitudinally extending with respect to such limb to prevent bending of such limb.

14. The intravenous injection shield assembly of claim 9, wherein said fastening means consist of synthetic materials which adhere when pressed together.

15. The intravenous injection shield assembly of claim 9, wherein said assembly further includes closure means for holding said second edge of said protective shield member adjacent to said second side wall.

16. The intravenous injection shield assembly of claim 15, wherein said closure means consists of a latch positioned on said base member and a cavity defined by said second edge of said protective shield member.

17. The intravenous injection shield assembly of claim 9, wherein said assembly further includes intravenous tubing retaining means.

18. The intravenous injection shield assembly of claim 17, wherein said intravenous tubing retaining means includes at least one adhesive strip removably attached to said first edge of said protective shield member.

19. An improved intravenous injection shield assembly for positioning on a limb comprising, in combination:
a base member having a substantially planar upper surface and a lower surface, said base member defining a plurality of strap openings;
a first side wall and a second side wall, said first and second side walls each being joined to said upper surface of said base member in an opposed relationship to one another;
a laterally flexible protective shield member having an uppermost surface, a first edge and a second edge;
at least two adjustable strap members each having a limb contact portion and a base member contact portion, each of said strap members extending through said plurality of strap openings;
fastening means positioned on each of said strap members and said base member for holding the shield assembly in a predetermined position on such limb;
whereby when the shield assembly is positioned on such limb, said portions of said strap members which are adapted for contact with the upper surface of such limb are in contact with the upper surface of such limb and said base member contact portions of said strap members are in contact with the lower surface of said base member, said first and second edges of said protective shield member being adjacent to said first and second side walls, respectively, said protective shield is positioned over the upper surface of such limb, said uppermost surface of said protective shield member being in a spaced apart relationship with the upper surface of such limb such that an intravenous needle and tubing can be positioned in the space defined between the uppermost surface of said protective shield member and the upper surface of such limb.

20. The intravenous injection shield assembly of claim 19, wherein said base member, first and second side walls and protective shield member consist of a rigid transparent plastic material.

21. The intravenous injection shield assembly of claim 19, wherein a fabric protection pad is mounted on said upper surface of said base member to protect such limb.

22. The intravenous injection shield assembly of claim 19, wherein said protective shield member includes at least one opening on said uppermost surface of said shield member, said opening allowing air to pass through said opening into the space defined between the uppermost surface of said shield member and the upper surface of such limb.

23. The intravenous injection shield assembly of claim 19, wherein said assembly is longitudinally extending with respect to such limb to prevent bending of such limb.

24. The intravenous injection shield assembly of claim 19, wherein said fastening means consist of synthetic materials which adhere when pressed together.

25. The intravenous injection shield assembly of claim 19, wherein said assembly further includes closure means for holding said first and second edges adjacent to said first and second side walls, respectively.

26. The intravenous injection shield assembly of claim 25, wherein said closure means consist of adhesive strips removably attached to said first and second edges of said protective shield member and first and second side walls, respectively.

27. The intravenous injection shield assembly of claim 19, wherein said assembly further includes intravenous tubing retaining means.

28. The intravenous injection shield assembly of claim 27, wherein said intravenous tubing retaining means consist of adhesive strips removably attached to either said first or second edges of said protective shield assembly.

* * * * *